United States Patent [19]

Toomey, Jr.

[11] Patent Number: 5,002,641
[45] Date of Patent: Mar. 26, 1991

[54] ELECTROCHEMICAL SYNTHESIS OF NIACIN AND OTHER N-HETEROCYCLIC COMPOUNDS

[75] Inventor: Joseph E. Toomey, Jr., Indianapolis, Ind.

[73] Assignee: Reilly Industries, Inc., Indianapolis, Ind.

[21] Appl. No.: 534,863

[22] Filed: Jun. 28, 1990

[51] Int. Cl.$^5$ ............................................... C25B 3/02
[52] U.S. Cl. ..................................................... 204/78
[58] Field of Search ........................................... 204/78

[56] References Cited

U.S. PATENT DOCUMENTS

| | | | |
|---|---|---|---|
| 2,413,099 | 12/1946 | Mueller | 295/10 |
| 2,437,938 | 3/1948 | Cislak et al. | 546/320 |
| 2,449,906 | 9/1948 | Mueller | 546/320 |
| 2,453,701 | 11/1948 | Conn et al. | 204/78 |
| 2,512,483 | 6/1950 | Conn | 204/78 |
| 2,513,251 | 6/1950 | Porter et al. | 546/320 |
| 4,212,711 | 7/1980 | Halter et al. | 204/78 |
| 4,482,439 | 11/1984 | Toomey, Jr. | 204/78 |
| 4,693,793 | 9/1987 | Alfenaar et al. | 204/78 |
| 4,750,978 | 6/1988 | Daniels | 204/78 |
| 4,759,834 | 7/1988 | Thomas et al. | 204/78 |

FOREIGN PATENT DOCUMENTS 17003 of 1914 United Kingdom .

OTHER PUBLICATIONS

Chem. Abstract, 82:170627v, Kostromin et al.
Chem. Abstract, 71:30331s, Stefanescu et al.
Woodward, Badgett and Kaufman, *Ind. Eng. Chem.*, vol. 36, No. 6, (1944), p. 544.
Black, Depp and Corson, *J. Org. Chem.*, vol. 14, 14, (1949).
Lovrecek, *Radovi Jugoslav. Akad. Znanosti i Umjetnosti* 296, 65-83, (1953).
Plattner, Keller, and Boller, *Helv. Chim. Acta.*, 37, 1379-92, (1954).
Bengtsson, *Acta. Chem. Scand.*, 9, 832-36, (1955).
Kucharaczyk and Zvakova, *Collection Czech. Chem. Commun.*, 28, 55-60, (1963).
Yokoyama, *Bull. Chem. Soc., Japan*, 7, 69-72, (1932).
Fichter and Stenzl, *Helv. Chim. Acta.* 19, 1171, (1936).
Kruglikov and Khomyakov, *Tr. Mosk. Khim.-Teknol. Inst.*, 1961, (32), 194.
Yokoyama and Yamamoto, *Bull Chem. Soc. Japan*, 18, 121, (1943).
Khomyakov, Bakhchisaraits'yan Tioshin, Kruglikov and Kazakova, *Tr. Mosk. Khim.-Teknol. Inst.*, (32), 249, (1961).
Khomyakov and Borkhi, *Tr. Vses. Nauch.-Issled. Instl. Khim. Reakivov Osobo Chist. Khim. Veshchestv*, 29, 226, (1966).
Borkhi and Khomyakov, *Khim. Geterotsikl Soedin*, 1967 (1), 167.
Kulka, *J. Am. Chem. Soc.* 68, 2472 (1946).
Khomyakov and Kruglikov, *Trudy Moskov. Khim.-Teknol. Inst. im. D. I. Mendeleeva*, (25), 178 (1957).
Khomyakov, Kruglikov and Berezovskii, *Zhur, Obshchei Khim.*, 28, 2898 (1958).
Krugilkov and Khomyakov, *Tr. Mosk. Khim.-Teknol. Inst.* 1961, (32), 201.
Khomyakov, Kruglikov, and Kazakova, *Tr. Mosk. Khim.-Teknol. Inst.* 1961 (32), 189.
Cochran and Little, *J. Org. Chem.* 26, 808 (1961).
Borkhi and Khomyakov, *Izobret. Prom. Obraztsy, Tovarnye Znaki* 43, (20), 38, 1966.
Borkhi, *Khim. Geterotsikl Soedin* 1970 (10), 1362 (1970).
Nankov and Yankov, *Elektrokhimiya* 7, (12), 1865, (1971).
Ito and Kawada, *Ann. Rept. Takamine Lab.*, 5, 14 (1953).
*J. Pharm. Soc. Japan*, 70, 156 (1950).

*Primary Examiner*—John F. Niebling
*Assistant Examiner*—Steven P. Marquis
*Attorney, Agent, or Firm*—Woodard, Emhardt, Naughton, Moriarty & McNett

[57] ABSTRACT

An electrochemical oxidation of a pi-deficient N-heterocyclic precursor compound having an oxidizable organic group attached by a carbon-to-carbon linkage. This precursor compound is at least sparingly water soluble. The preferred electro-oxidation is conducted at an effective anode and in a medium which consists essentially of water, carboxylic acid, and the precursor compound. Preferred are electro-oxidations of substituted pyridine and quinoline bases and a particularly preferred aspect provides a convenient electrochemical synthesis of niacin from 3-methylpyridine.

30 Claims, No Drawings

ELECTROCHEMICAL SYNTHESIS OF NIACIN AND OTHER N-HETEROCYCLIC COMPOUNDS

BACKGROUND OF THE INVENTION

This invention resides generally in the fields of N-heterocyclic and electrochemistry, and in a preferred aspect provides a convenient and commercially practicable electrochemical oxidation of pyridine bases to corresponding carboxylic acids such as niacin.

In this regard, pyridinecarboxylic acids are useful inter alia as chemical intermediates and corrosion inhibitors. Further, one such acid identified as 3-pyridinecarboxylic acid (also known by the names Vitamin B-3, nicotinic acid and niacin) has particular value as an essential vitamin. Its importance in the human diet, for example, led in the 1940's to niacin fortification of wheat flour and other consumer products. The adoption and continuation of this practice has generated steady demand for niacin and a concomitent driving force for improved methods to produce this and other pyridinecarboxylic acids. Moreover, recent reports that niacin may help reduce cholesterol levels in the blood have sparked an even greater demand for improved synthetic processes in this area.

As background respecting these processes, early oxidations of pyridine derivatives such as methylpyridines were conducted using chemical oxidizing agents and catalysts. More recent investigations have included these chemical methodologies in addition to attempts at electrochemical oxidations.

Accordingly, reports relating to chemical oxidizing agents dating back over a hundred years disclose forming niacin by partial oxidation of nicotine with nitric acid, potassium permanganate or potassium dichromate. See Woodward, Badgett and Kaufman, *Ind. Eng. Chem.*, Vol. 36, No. 6, (1944) p. 544 and sources cited therein. Studies using these chemical oxidizing agents have continued, for instance, with potassium permanganate oxidations of alkylpyridine bases being reported by Black, Depp and Corson, *J. Org. Chem.*, Vol. 14, 14 (1949); by Lovrecek, *Radovi Jugoslav. Akad. Znanosti i Umjetnosti* 296, 65–83 (1953); and by Plattner, Keller, and Boller, *Helv. Chim. Acta.* 37, 1379–92 (1954). These reactions have suffered, however, in that they have generally caused excessive oxidation and resultant ring degradation, particularly with polyalkylpyridines. Likewise, Bengtsson, *Acta. Chem. Scand.* 9, 832–36 (1955) reports nitric acid oxidations of pyridine homologs which has proven a more economic route, but nevertheless requires undesirably high temperatures and pressures which can cause decarboxylation or loss of carbon dioxide from the resulting product.

Other reported chemical methodologies have included oxidation of pyridine derivatives with ozone, ozonized oxygen or ozonized air [G. B. Patent No. 17,003], and also oxidation by action of sulfuric acid in the presence of a selenium compound. U.S. Pat. Nos. 2,449,906 and 2,513,009. Additionally, U.S. Pat. No. 2,513,251 reports oxidation of pyridine derivatives by reaction with nitrogen tetraoxide in a sulfuric acid medium.

Still other chemical routes to this end have included catalytic air oxidations of pyridine derivatives, [U.S. Pat. No. 2,437,938 and Kucharczyk and Zvakova, *Collection Czech. Chem. Commun.* 28, 55–60 (1963)], as well as oxidations using electro-generated superoxide ion. Sagae, Fujihira, Lund and Osa, *Heterocycles*. Vol. 13 (1979), p. 13. Additionally, Woodward, Badgett and Kaufman, *Ind. Eng. Chem.*, Vol. 36, No. 6, (1944), p. 544 reports catalytic oxidation of pyridine derivatives in sulfuric acid using mercuric sulfate and bismuth trinitrate catalysts (with moderate success), and selenium, selenium dioxide, and copper selenite catalysts (with greater success).

As noted above, another general area of study in this field has been that of electrochemical oxidation. This discipline had its nascence in 1932 when electrochemical oxidations of 2-methylpyridine and nicotine to 2-pyridinecarboxylic acid and nicotinic acid, respectively, were first reported. Yokoyama *Bull. Chem. Soc. Japan* 7, 69–72 (1932) and Yokoyama, ibid, 7 103-S (1932). These early electrochemical oxidations occurred in a sulfuric acid medium at a lead anode. Reports have since been made through the years of electrochemical oxidations of various pyridine derivatives with varying levels of success, but these oxidations have consistently occurred in moderate or better yields only in highly acidic mediums having substantial mineral acid components.

For example, the following sources report formation of the named pyridinecarboxylic acids upon electrochemical oxidation of pyridine derivatives in mediums containing sulfuric acid and at anodes of lead or lead-dioxide, or in fewer cases platinum: (1) Nicotinic acid from nicotine, Fichter and Stenzl, *Helv. Chim. Acta.* 19, 1171 (1936); (2) Nicotinic acid from 3-methylpyridine, Kruglikov and Khomyakov, *Tr. Mosk. Khim.-Teknol Inst.* 1961 (32), 194; (3) Quinolinic acid from quinoline, Yokoyama and Yamamoto, *Bull Chem. Soc. Japan* 18, 121 (1943); Khomyakov, Bakhchisaraits'yan, Tioshin, Kruglikov and Kazakova, *Tr. Mosk. Khim.-Teknol. Inst.* (32), 249 (1961); Khomyakov and Borkhi, *Tr. Vses. Nauch.-Issled. Inst. Khim. Reakivov Osobo Chist. Khim. Veshchestv* 29, 226 (1966); Khomyakov, Bzbanovskii and Borkhi, ibid. 29, 304 (1966); Borkhi and Khomyakov, *Khim. Geterotsikl Soedin* 1967 (1), 167; and Tsodikov, Borkhi, Brudz, Khomutov and Khomyakov, ibid. 1967 (1) 112; (4) Nicotinic acid from 3-methylpyridine, and quinolinic acid from quinoline, Kulka, *J. Am. Chem. Soc.* 68, 2472 (1946); U.S. Pat. No. 2,512,483; Khomyakov and Kruglikov, *Trudy Moskov. Khim.-Teknol. Inst. im. D. I. Mendeleeva* (25), 178 (1957); and Khomyakov, Kruglikov and Berezovskii, *Zhur. Obshchei Khim.* 28, 2898 (1958); (5) Quinolinic acid from sulfonated quinoline, U.S Pat. No. 2,453,701; (6) Isonicotinic acid from the methylol derivative of 4-picoline, Krugilkov and Khomyakov, *Tr. Mosk Khim.-Teknol. Inst.* 1961 (32), 201; (7) Lutidinic acid from 2,4-lutidine, Khomyakov, Kruglikov, and Kazakova, *Tr. Mosk. Khim.-Teknol. Inst.* 1961 (32), 189; (8) Monosubstituted pyridinedicarboxylic acids from monosubstituted quinolines, Cochran and Little, *J. Org. Chem.* 26, 808 (1961); (9) Isocinchomeronic acid from 2-methyl-5-ethylpyridine, Borkhi and Khomyakov, *Izohret. Prom. Obraztsy, Tovarnye Znaki* 43 (20), 38 (1966); and Borkhi, *Khim. Geterotsikl Soedin* 1970 (10), 1362 (1970); and (10) Isonicotinic acid from 4-ethylpyridine, Nankov and Yankov, *Elektrokhimiya* 7 (12), 1865 (1971).

In addition, electrolytic oxidations of 4-methylpyridine in 20% nitric acid and 20% sulfuric acid mediums at platinum and lead dioxide anodes are reported by Ito and Kawada, *Ann. Rept. Takamine Lab.* 5, 14 (1953), as are oxidations of 4-ethylpyridine in these two mediums at a platinum anode. These same two authors also report another experiment in which an extremely poor yield resulted from an electrolytic oxidation of 4-methylpyridine in an alkaline bath. Similarly, U.S. Pat. No. 4,750,978 reports low product yields resulting from electrolytic oxidations of 2-methyl-3-quinolinecarboxylic acid in 15% aqueous NaOH baths, and Ochiai and Okuda report very poor yields resulting from the electrolytic oxidation of 2-picoline in alkaline (10% yield) and neutral (10% yield) baths in *J Pharm. Soc Japan,* 70, 156 (1950).

Addressing generally these processes discussed above, both chemical and electrochemical, they present problems and inconveniences on a laboratory scale which are multiplied greatly in commercial scale reactions. Catalytic oxidations often require expensive catalysts and/or oxidizing agents and long reaction times, require the use of high temperatures and pressures, and present difficulties in processing and recovering reaction products. Moreover, in several of the chemical processes, ring degradation and accompanying product losses result from excessive oxidation.

The electrochemical processes, on the other hand, generally avoid use of expensive chemical catalysts and oxidants and thus hold greater promise in these respects for providing economical routes to pyridinecarboxylic acids. Nevertheless, commercial and technical development of economic electrochemical processes in this area has seriously lagged to date, with most reports being largely the result of qualitative study. The applicant's own earlier U.S. Pat. No. 4,482,439 discloses a commercially-viable electrochemical oxidation of pyridine bases performed in a flow cell having either an anion - or cation-selective ion-exchange membrane divider at a lead dioxide anode and in an aqueous medium comprising sulfuric acid in at least a 1:1 equivalent ratio with the pyridine base in solution. This flow cell process provides excellent yields and constitutes a significant improvement over the prior art at the time. As in the many other reported electro-oxidations achieving notable yields, however, this process too is performed in a medium containing a substantial mineral acid (sulfuric acid) component. This presents disadvantages in that effective recovery of the carboxylic acid product from such mediums requires pH neutralization which can particularly cumbersome and expensive on a commercial scale.

Further, simple workups of electrolysis products are essential in commercial settings as in many cases more than half of the total synthesis investment is devoted to this procedure. Auxilliary salts which serve as electrolytes but complicate the workup procedure can thus lead to pronounced increases in manufacturing costs. See generally, *Techniques of Chemistry.* (N. L. Weinberg and B. V. Tilak ed.), p. 279, John Wiley & Sons (1982). Accordingly, an electrochemical process which would allow one to eliminate or at least substantially reduce the use of such auxilliary salts would provide great advantage in commercial settings.

It is in light of this extensive background that the applicant began his work to discover a convenient and effective commercial process to satisfy the continuing and increasing demand for these carboxylic acids, including of particular interest niacin for the reasons stated above. By this work the applicant has now succeeded in providing with this invention a commercially and technically important electrochemical process for oxidizing pyridine and other N-heterocyclic compounds.

SUMMARY OF THE INVENTION

Accordingly, one preferred embodiment of this invention relates to an improved electrochemical oxidation of a pi-deficient N-heterocyclic precursor compound (e.g. a pyridine or quinoline derivative). The precusor compound has an oxidizable organic group attached by a carbon-to-carbon linkage, and is at least sparingly water soluble. The preferred oxidation is conducted at an effective anode and in a medium consisting essentially of water, a carboxylic acid, and the precursor compound.

In another preferred aspect of the invention, the medium in which the electrochemical oxidation occurs is also substantially free from mineral acid while achieving good yields. Additionally, in the applicant's preferred work to date, the precursor compound has been oxidized to a corresponding carboxylic acid or ketone product, and substituted pyridine and quinoline bases have been preferred precursor compounds. A particularly preferred aspect provides an electrochemical synthesis of niacin from 3-methylpyridine. Importantly, and in contrast to the prior art electrochemical processes in this area, the applicant's preferred oxidations have occurred in these simplified mediums while achieving high current efficiencies, reactant solubility, and electrolyte conductivities without the need of adding mineral acid or other conductive salts.

Without restricting the invention, it is believed that these advantages may result from salt formation between the precursor compounds and the carboxylic acid in the medium thereby providing excellent water solubility of both and as well a salt which acts beneficially as an electrolyte in the medium. Additionally, this salt acts as a buffer, thus stabilizing the pH of the medium during the reaction. In any case, the applicant's preferred electro-oxidations carry significant advantages over prior art processes. For instance, they require no pH neutralization of the electrolytic medium to effectively recover carboxylic acid product and also provide for simplified electrolyte mediums not requiring auxilliary salts other than the salt formed between the carboxylic acid and precursor compound. Consequently, use of such auxilliary salts can be eliminated or, if used, their concentrations can be substantially reduced which simplifies workup procedures.

Other preferred embodiments of this invention relate to additional processes and electrochemical baths capitalizing on the applicant's preferred electrochemical mediums and other discoveries as set forth herein. Additional objects and advantages of this invention will become apparent upon reading the description that follows.

DESCRIPTION OF THE PREFERRED EMBODIMENT

As stated above, one preferred embodiment of this invention relates to an electrochemical oxidation of a pi-deficient N-heterocyclic precursor compound such as, for example, a pyridine or quinoline derivative. The precursor compound has an oxidizable organic group attached by a carbon-to-carbon linkage. This precursor compound also is at least sparingly water soluble. Additionally, the electro-oxidation occurs at an effective anode and in a medium consisting essentially of water, a carboxylic acid, and the precursor compound As used herein, the phrase "electrochemical oxidation" is meant to include all possible variations as to reaction conditions and the like which are known to those of ordinary skill in the art to which this invention pertains. For instance, the electrochemical oxidation of the invention can occur in all possible electrochemical cell configurations including divided or undivided, mixed or unmixed, and also flow cells in addition to "tank" or "beaker" type cells. The only exceptions to this relate to any specific conditions or features which have shown to be required from applicant's testing to date which are further detailed herein. Additionally, the term "sparingly water soluble" is commonly used and well known in the art, and as used herein connotes compounds which are preferably at least about 0.01 weight percent soluble in water.

As to specific materials, conditions and processing steps, the applicant's preferred oxidations to date have been performed at effective anodes which, under the further conditions of the invention, have oxidized the precursor compounds, preferably to their corresponding carboxylic acids or ketones. Thus, where the product is carboxylic acid, effective anodes will result in an observed increase in the total carboxylic acid component in the medium. To date preferred effective anode materials have included graphite, carbon, or a metal or metal oxide of palladium, platinum, irridium, ruthenium, chromium, molybdenum, tin, cerium or manganese. Of course, anode materials containing mixtures of these substances with each other or with other suitable materials are also appropriate. Further, it is contemplated that other effective anode materials also performing in this manner are acceptable for and within the scope of this invention.

Additionally, the physical and morphological characteristics of the electrodes, while having somewhat influenced results, have not to date shown to be critical. Accordingly, all physical and morphological electrode forms including, for instance, polymer coated or metal or metal oxide surface coated electrodes, are similarly contemplated as being within the scope of the invention. Also, in the case of noble metals or metal-oxides they are preferably supported on inert conductive supports. Further, the addition of metals, metal oxides or metal salts to the electrolyte as soluble species is also acceptable for catalyzing the intended chemistry or for providing mediators for electron transfer. These may be chosen to include the metals or metal oxides listed above as possible anode materials as well as others as known in the art.

Although the composition of the cathode used in the cell has not proven to be critical to date, the particular cathode materials used have to some extent influenced results. The preferred cathode materials have thus far exhibited hydrogen overpotentials not substantially exceeding those which would be predicted by the accepted Nernst equation (i.e. not high-hydrogen-overpotential cathodes), with cathodes comprising graphite, platinum, iron, steel or titanium having been found more preferred to this point.

Similarly, electrochemical cell configuration has not shown to be critical to date; however, preferred electrochemical oxidations are conducted in cells preferably divided using porous dividers such as ceramic, glass frit, and porous plastics, or ion-exchange membranes (either anion or cation selective). Additionally, in this vein, cell voltages up to about 20 V have proven appropriate for the applicant's preferred oxidations, with about 4-10 V cells being preferred up to this point.

As to precursor compounds, the applicant's preferred processes have involved electro-oxidation of pi-deficient N-heterocyclic compounds which are at least sparingly water soluble. In a preferred aspect, these compounds also have a pKa of at least about 4. The term "pi-deficient N-heterocyclic compound" describes a cyclic compound which contains one or more nitrogen atoms in the ring where the lone pair of electrons on at least one of those nitrogen atoms is available to undergo reactions typical of organic nitrogen bases. Pi-deficiency has been found to be necessary in the compounds oxidized by applicant's preferred electrochemical processes, and it is believed that this is because this ensures that the substrates are basic enough to form salts with the carboxylic acid in the medium and to form conductive salts. Pi-deficient N-heterocylic compounds include pyridines, pyrimidines and quinolines, as well as other perhaps less common chemical compounds which possess substantially the same properties as pyridine and quinoline compounds and are equivalents thereof such as diazines and triazines. Although many pi-deficient N-heterocycles are six-membered cyclic compounds, five-membered cyclic compounds with two or more nitrogen atoms are also pi-deficient, such as imidazoles or other diazoles or triazoles.

In another aspect, preferred electro-oxidations involve pi-deficient N heterocyclic precursor compounds according to the general formula:

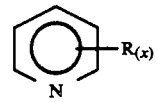

wherein, x=1-3; and R=——CH³,
a primary or secondary alkyl group having about 2-6 carbon atoms,
a cycloalkyl group having about 3-6 carbon atoms,
an aralkyl group of the formula [——($CH_2)_n$——aryl] where n=1-3,
——$(CH_2)_m$COR' or ——$(CH_2)_m$CHOHR' where m=0-5 and R'=H or an alkyl group having about 1-6 carbon atoms, or a cycloalkyl, aryl or aralkyl group having about 3-10 carbon atoms;
and wherein two adjacent R groups on the ring taken together may be a fused cycloalkyl or fused aryl group.

More preferred precursor compounds have been mono- and dialkylpyridine bases, wherein the alkyl group is preferably lower alkyl, such as methyl, ethyl, propyl, butyl, etc., with a particularly preferred aspect of the invention being an electro-oxidation of 3-methylpyridine to niacin.

As to the rate of charge passed through the cell, optimization of current densities will depend on the particular medium and cell configurations selected, and is well within the skill of those working in this area. However, in the applicant's preferred oxidations, current has preferably been passed in amounts sufficient to achieve current densities ranging from about 1 to about 400 mA/cm². Further, in the particularly preferred oxidations of 3-methylpyridine to niacin, current has been passed in amounts sufficient to achieve current densities of about 10 to about 100 mA/cm².

In addition, the total amount of charge passed through the cell will, of course, depend upon the efficiency of electron transfer for the intended chemistry. Generally, however, the applicant's studies have shown that the charge passed should be limited to that just necessary to achieve maximum conversion of the precursor compound. Similarly, temperatures have not proven critical in the applicant's studies with temperatures of about minus 20° C. up to the reflux temperatures of the electrolytes having proven appropriate to date.

Respecting the electrochemical medium of this preferred embodiment, in addition to the other requirements set forth herein, it has to date preferably exhibited a pH above about 2 and up to about 8, with a more preferred pH range being about 4–7. Additionally, the water, precursor compound, and carboxylic acid are preferably included in amounts whereby the particular precursor compound and carboxylic acid used each constitute at least about 5 weight % of the medium. More preferred systems include the precursor compound and carboxylic acid each constituting about 10% by weight or greater of the medium. Additionally, the most preferred oxidations of precusor compounds to carboxylic acids have been conducted in mediums having levels of carboxylic acid approaching or even exceeding saturation point. In this manner, as charge is passed through the cell, corresponding carboxylic acid has been formed in amounts whereby carboxylic acid precipitates from the medium as its saturation point therein is exceeded. This enables an extraordinarily convenient recovery of the corresponding carboxylic acid product from the medium.

In a further aspect, preferred oxidations to carboxylic acids have been conducted in mediums wherein the corresponding carboxylic acid of the precursor compound constitutes all or at least a substantial component of the total carboxylic acid in the medium. In this way, a precipitate of corresponding carboxylic acid of increased purity has been obtained.

In the case of the applicant's particularly preferred electrochemical synthesis of niacin, the medium has preferably contained water and 3-methylpyridine in a weight ratio from about 1:0.01 to about 1:4. It has additionally been preferred that these mediums be saturated in niacin.

In other facets of the invention, preferred mediums are substantially free from the mineral acids predominantly used in the prior art. Additionally, preferred mediums have demonstrated conductivities of at least about 500 micro-Seimens (reciprocal millionths of an ohm) per centimeter (cm) as reported further hereinbelow.

As stated above, other preferred embodiments of this invention relate to additional electrochemical processes as well as electrochemical baths which provide significant advantages corresponding to those discussed hereinabove. In this regard, one preferred embodiment of the invention relates to a process for electrochemically oxidizing a precursor compound as described herein wherein the oxidation is conducted in an aqueous electrolyte. In accordance with this embodiment significant improvements and advantages are provided by the step of initially charging the electrolyte with an effective amount of a carboxylic acid to significantly enhance water solubility of the precursor compound. What constitutes an effective amount in this respect varies according to the particular chemistries involved. However, the applicant's studies to date have shown that the addition of about 2% by weight of the precursor's corresponding carboxylic acid is more than enough to significantly enhance water solubility of the precursor compound. Additional preferred aspects of this preferred embodiment correspond to those discussed in the embodiment above.

Another preferred embodiment, as stated, involves an improved electrochemical bath capitalizing on the applicant's preferred electrochemical mediums described herein and thereby providing significant advantages and advancements over the prior art.

Reference will now be made to specific examples for the purpose of further describing and understanding the features of the applicant's preferred embodiments and in addition their advantages and improvements over the art. It is understood, however, that these examples are representative only, and that such additional embodiments and improvements of the same are within the contemplation and scope of the applicant's invention as would occur to one of ordinary skill in this art.

EXAMPLE 1

Electrochemical Oxidation of Beta-Picoline

An electrolyte medium was prepared containing 87 parts water by weight, 8 parts beta-picoline, and 5 parts niacin. The solution was charged into an undivided cell and electrolyzed using an anodized tin anode with a platinum cathode at a constant current between 0.1 and 1.0 A (10–100 mA/sq. cm). Analysis of the electrolyte indicated an increase in niacin corresponding to a 75% current efficiency. An analogous oxidation was also performed except current was continuously passed until niacin precipitated from the medium as it was formed, and as its saturation point was exceeded

EXAMPLE 2

Electrochemical Oxidation of Beta-Picoline

In this Example a carboxylic acid other than the corresponding carboxylic acid was used in the medium. Accordingly, an electrolyte medium was prepared and electrolyzed as initially in Example 1 except acetic acid was used in the place of niacin. The electrolyte was analyzed and indicated an increase in niacin corresponding to a 61% current efficiency.

EXAMPLE 3

Electrochemical Oxidation of Alpha-Picoline

An electrolyte was prepared containing 85 parts by weight water, 10 parts aloha-picoline, and 5 parts picolinic acid. The solution was electrolyzed as initially in Example 1 above to give an increase in picolinic acid corresponding to 83% current efficiency.

EXAMPLE 4

Electrochemical Oxidation of 3,5-Lutidine

The experiment was performed as initially in Example 1 above, except 3,5-lutidine was substituted for the beta-picoline and dinicotinic acid was substituted for the niacin used to prepare the initial electrolyte medium. The medium was electrolyzed and thereafter contained dinicotinic acid in increased amounts indicating a 68% current efficiency.

EXAMPLE 5

Electrochemical Oxidation of 2,3-Lutidine 2,3-Lutidine and quinolinic acid were used according to the general initial procedure of Example 1 above. Increased quinolinic acid concentration after electrolysis corresponded to an 87% efficiency.

EXAMPLE 6

Electrochemical Oxidation of 2-Methylquinoline

An electrolyte medium was prepared containing 89 parts water by weight, 5 parts 2-methylquinoline, and 6 parts quinoline-2-carboxylic acid. The medium was charged into an undivided cell and electrolyzed using a molybdenum anode and a platinum cathode at a constant current between 0.05 and 1.5 A (5–150 mA/cm$^2$). Analysis of the electrolyte indicated a 93% current efficiency in the production of quinoline-2-carboxylic acid.

EXAMPLES 7 and 8

Electrochemical Oxidations of 2-Methylquinoline in Divided Cells

In two parallel experiments, either an anion-exchange membrane or a cation-exchange membrane was used to divide the electrochemical cell. The anolyte solution was prepared as described in Example 6 above. The catholyte solution consisted of dilute sodium sulfate and a small amount of added sulfuric acid. When the anion-exchange membrane was used, additional sulfuric acid had to be added to the catholyte to compensate for the sulfate anions transferred through the membrane to the anolyte compartment.

Analysis of the reacted electrolytes indicated current efficiencies greater than 85% in the production of quinoline-2-carboxylic acid. While cation-exchange membranes are generally preferred, the choice between anion- and cation-exchange membranes depends on the composition of the catholyte. For example, anion-exchange membranes are sometimes preferred including in some processes wherein hydroxide anion is transferred from the catholyte to the anolyte.

EXAMPLE 9

Electrochemical Oxidation of 4-Acetylpyridine

An electrolyte medium was prepared containing 90 parts water by weight, 7 parts 4-acetylpyridine, and 3 parts isonicotinic acid. The solution was charged into an undivided cell and electrolyzed using a palladium anode and a platinum cathode at a constant current density. Analysis of the electrolyte indicated a 98% current efficiency. Isolation of the acid by precipitation at the isoelectric point (pH approx. 3.0 to 3.5) gave an 89% yield of isonicotinic acid (the weight of the isonicotinic acid present at the start of the electrolysis was subracted out of the total weight yield to determine the chemical yield efficiency)

EXAMPLE 10

Electrochemical Oxidation of 2-Benzylpyridine

An electrolyte medium was prepared containing 85 parts water by weight, 5 parts 2-benzylpyridine, and 10 parts picolinic acid. The solution was charged into an undivided cell and electrolyzed at a molybdenum anode with a graphite cathode at a constant current density between 0.1 and 1.0 A (10–100 mA$^2$ cm.). Analysis of the electrolyte indicated an 88% current efficiency for the production of 2-benzoylpyridine.

EXAMPLE 11

Water/Beta-Picoline/Niacin Mediums

To study the physical and electrochemical properties of various medium compositions, mixtures of beta-picoline and water were prepared and then saturated with added niacin by stirring at 25° C. for at least 17 hours. The mixtures were thereafter thermostated in a water bath for one day. Conductivity was then determined with a Yellow Springs Instrument's Model 31 Conductivity Bridge, and the amount of niacin in the solution was analyzed by titration with sodium hydroxide. The results are given in Table 1 below in which all percentages are expressed as weight-to-weight percent in the final saturated solution, and conductivity is expressed as micro-Seimens (reciprocal millionths of an ohm) per centimeter.

TABLE 1

| Medium | Water (%) | Picoline (%) | Niacin (%) | Conductivity (microS/cm) |
|---|---|---|---|---|
| a | 98.45 | 0.00 | 1.55 | 300 |
| b | 80.36 | 8.92 | 10.72 | 12000 |
| c | 67.37 | 16.84 | 15.79 | 15000 |
| d | 57.20 | 24.52 | 18.28 | 13000 |
| e | 48.43 | 32.29 | 19.28 | 10000 |
| f | 40.67 | 40.67 | 18.66 | 8000 |
| g | 32.88 | 49.32 | 17.80 | 5000 |
| h | 25.33 | 59.11 | 15.56 | 3000 |
| i | 17.34 | 69.35 | 13.31 | 1200 |
| j | 8.83 | 79.49 | 11.68 | 210 |
| k | 0.00 | 89.21 | 10.79 | 12 |

The results presented in Table I demonstrate the significance of the applicant's discovery and highlight the magnitude of its advantages over the prior art processes in achieving commercially practicable electrochemical syntheses of N-heterocyclic compounds. Excellent conductivities and reactant solubilities were exhibited in simple carboxylic acid, precursor, and water mediums. For example, medium "b" containing water, niacin and a moderate amount (8.92 weight %) of picoline demonstrated a conductivity of 12000 microS/cm. This represents a forty fold increase over the 300 microS/cm conductivity of medium "a" containing only niacin and water. In addition, mediums "c" and "d" appear particularly favorable in that they provide excellent conductivity as well as solubility of the precursor compound. In this regard, the selection and optimization of electrolyte mediums will depend upon a balancing of these and other factors as will be apparent to those experienced in this field.

EXAMPLE 12

Water/Gamma-Picoline/Isonicotinic Acid Mediums

Solubility of the isonicotinic acid in pure water was measured as less than 1 wt %. Impressively, isonicotinic acid formed a saturated solution at 21 wt% acid, 35 wt% water, and 39 wt% gamma-picoline.

EXAMPLE 13

Water/Alpha-Picoline/Picolinic Acid Mediums

Conductivity of aloha-picoline/water solutions having more than 10 wt% water was less than 150 micro-Seimens/cm. To the contrary, a conductivity of 24500 micro-Seimens/cm was measured for a 3-component system in which picolinic acid was miscible in mixtures of water/alpha-picoline having more than 10 wt% water.

EXAMPLE 14

Water/2,4-Lutidine/Lutidinic Acid Mediums

A medium of 66 wt% water and 33 wt% 2,4-lutidine was prepared and found largely heterogeneous. Surprisingly, an addition of only 2 wt% lutidinic acid caused the medium to become homogeneous. Further lutidinic acid was added to form a solution of 26 wt% diacid, 25 wt% 2,4-lutidine, and 49 wt% water, which demonstrated a conductivity of 13000 micro-Seimens/cm.

EXAMPLE 15

Water/2,3-Lutidine/Quinolinic Acid Mediums

A medium of 66 wt% water and 33 wt% 2,3-lutidine was prepared and also found substantially heterogeneous, whereafter addition of only 2 wt% quinolinic acid caused considerable solublization of the 2,3-lutidine. Additional quinolinic acid was added to form solutions of greater than 25 wt% diacid, 25 wt% 2,3-lutidine, and 50 wt% water (conductivity 11000 micro-Seimens/cm). Additionally, it was noted that the presence of 2,3-lutidine significantly increased the solubility of quinolinic acid in water.

EXAMPLE 16

Comparative Study of a Non-N-Heterocyclic Compound ortho-Toluidine was found essentially insoluble in water. Addition of anthranilic acid did not increase water solubility of either component, thus demonstrating the necessity of an N-heterocyclic precursor compound to achieve the significant advantages of the invention.

I claim:

1. In an electrochemical oxidation of a pi-deficient N-heterocyclic compound, said compound having an oxidizable organic group attached by a carbon-to-carbon linkage and being at least sparingly water soluble, the improvement comprising conducting said oxidation at an effective anode and in a medium consisting essentially of water, carboxylic acid, and said compound and wherein said medium is at least substantially free from mineral acid.

2. The electrochemical oxidation of claim 1 wherein during said conducting said medium has a pH of about 2 to about 8.

3. The electrochemical oxidation of claim 2 wherein said compound is a pyridine or quinoline derivative and wherein during said conducting said medium has a pH of about 4 to about 7.

4. The electrochemical oxidation of claim 1, 2 or 3 wherein during said conducting said anode comprises graphite, carbon, or a metal or metal oxide of palladium, platinum, iridium, ruthenium, molybdenum, tin, cerium, chromium or manganese.

5. The electrochemical oxidation of claim 4 wherein during said conducting the counter electrode to said anode is a cathode comprising graphite, platinum, or titanium.

6. The electrochemical oxidation of claim 1 wherein during said conducting said compound has the general formula:

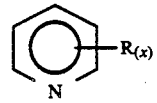

wherein, x=1–3; and R=—CH$_3$,
a primary or secondary alkyl group having about 2–6 carbon atoms,
a cycloalkyl group having about 3–6 carbon atoms
an aralkyl group of the formula [—(CH$_2$)$_n$—aryl] where n=1–3,
—(CH$_2$)$_m$COR' or —(CH$_2$)$_m$CHOHR' where m=0–5 and R'=H or an alkyl group having about 1–6 carbon atoms, or a cycloalkyl, aryl or aralkyl group having about 3–10 carbon atoms;
and wherein two adjacent R groups on the ring taken together may be a fused cycloalkyl or fused aryl group.

7. The electrochemical oxidation of claim 6 wherein during said conducting said medium has a pH of about 2 to about 8.

8. The electrochemical oxidation of claim 7 wherein during said conducting said medium has a pH of about 4 to about 7.

9. The electrochemical oxidation of claim 6 wherein during said conducting said anode comprises graphite, carbon, or a metal or metal oxide of palladium, platinum, iridium, ruthenium, molybdenum, tin, cerium, chromium or manganese.

10. The electrochemical oxidation of claim 9 wherein during said conducting said anode comprises molybdenum.

11. The electrochemical oxidation of claim 9 wherein during said conducting said anode comprises palladium.

12. The electrochemical oxidation of claim 9 wherein during said conducting said anode comprises tin.

13. The electrochemical oxidation of claim 9 wherein during said conducting said anode comprises chromium.

14. The electrochemical oxidation of claim 9 wherein during said conducting the counter electrode to said anode is a cathode comprising graphite, platinum, or titanium.

15. The electrochemical oxidation of claim 14 wherein during said conducting said medium has a pH of about 4 to about 7.

16. The electrochemical oxidation of claim 15 wherein during said conducting said medium has a conductivity of at least about 500 micro-seimens per centimeter.

17. The electrochemical oxidation of claim 16 wherein during said conducting current densities of about 1 mA/cm$^2$ to about 400 mA/cm$^2$ are applied to said cell.

18. The electrochemical oxidation of claim 17 wherein said compound is oxidized to a corresponding ketone.

19. The electrochemical oxidation of claim 17 wherein said compound is oxidized to a corresponding carboxylic acid.

20. The electrochemical oxidation of claim 19 wherein said medium contains said corresponding carboxylic acid at levels at least approaching saturation point.

21. The electrochemical oxidation of claim 20 wherein during said conducting a current efficiency approaching 60% or above is achieved.

22. The electrochemical oxidation of claim 21 wherein during said conducting said compound is a mono- or dimethylpyridine.

23. The electrochemical oxidation of claim 22 wherein during said conducting said methylpyridine is 3-methylpyridine and said corresponding carboxylic acid is niacin.

24. The electrochemical oxidation of claim 23 wherein during said conducting current densities of about 10 to about 100 mA/cm$^2$ are applied to said cell.

25. The electrochemical oxidation of claim 24 wherein during said conducting a current efficiency approaching 70% or above is achieved.

26. The electrochemical oxidation of claim 25 wherein during said conducting niacin is formed in amounts whereby it precipitates from the medium as its saturation point therein is exceeded.

27. The electrochemical oxidation of claim 26 wherein during said conducting said medium is substantially free from mineral acid.

28. In an electrochemical oxidation of a pi-deficient N-heterocyclic precursor compound having an oxidizable organic group attached by a carbon-to-carbon linkage, said compound being at least sparingly water soluble, and said oxidation being conducted in an aqueous electrolyte, the improvement comprising the step of:

initially charging said aqueous electrolyte with an effective amount of a carboxylic acid to significantly enhance water solubility of said precursor compound.

29. The electrochemical oxidation of claim 28 wherein during said charging said compound is a mono- or dimethylpyridine and said acid is a pyridinecarboxylic acid.

30. The electrochemical oxidation of claim 29 wherein during said charging said methylpyridine is 3-methylpyridine and said pyridinecarboxylic acid is niacin.

* * * * *

UNITED STATES PATENT AND TRADEMARK OFFICE
CERTIFICATE OF CORRECTION

Page 1 of 3

PATENT NO. : 5,002,641

DATED : March 26, 1991

INVENTOR(S) : Joseph E. Toomey, Jr.

It is certified that error appears in the above-identified patent and that said Letters Patent is hereby corrected as shown below:

In column 4, line 5, please delete "pi-deficient" and insert in lieu thereof --pi-deficient--.

In column 4, line 59, please delete "pi-deficient" and insert in lieu thereof --pi-deficient--.

In column 6, line 2, please delete "pi-deficient" and insert in lieu thereof --pi-deficient--.

In column 6, line 6, please delete "pi-deficient" and insert in lieu thereof --pi-deficient--.

In column 6, line 10, please delete "Pi-deficient" and insert in lieu thereof --Pi-deficient--.

In column 6, line 16, please delete "Pi-deficient" and insert in lieu thereof --Pi-deficient--.

In column 6, line 21, please delete "pi-deficient" and insert in lieu thereof --pi-deficient--.

In column 6, line 24, please delete "pi-deficient" and insert in lieu thereof --pi-deficient--.

In column 6, line 27, please delete "pi-deficient" and insert in lieu thereof --pi-deficient--.

In column 8, line 32 please insert a --.-- after the word exceeded.

UNITED STATES PATENT AND TRADEMARK OFFICE
CERTIFICATE OF CORRECTION

Page 2 of 3

PATENT NO. : 5,002,641

DATED : March 26, 1991

INVENTOR(S) : Joseph E. Toomey, Jr.

It is certified that error appears in the above-identified patent and that said Letters Patent is hereby corrected as shown below:

In column 8, line 48, please delete "aloha-picoline" and insert in lieu thereof --a<u>lpha</u>-picoline--.

In column 8, line 57, please delete "beta-picoline" and insert in lieu thereof --<u>beta</u>-picoline--.

In column 9, line 69, please delete "beta-picoline" and insert in lieu thereof --<u>beta</u>-picoline--.

In column 10, line 57, please delete "gamma-picoline" and insert in lieu thereof --<u>gamma</u>-picoline--.

In column 10, line 62, please delete "aloha-picoline" and insert in lieu thereof --<u>alpha</u>-picoline--.

In column 10, line 67, please delete "alpha-picoline" and insert in lieu thereof --<u>alpha</u>-picoline--.

In column 11, line 31, please delete "ortho-Toluidine" and insert in lieu thereof --<u>ortho</u>-Toluidine--.

In column 11, line 39, please delete "pi-deficient" and insert in lieu thereof --<u>pi</u>-deficient--.

In column 14, line 1, please delete "pi-deficient" and insert in lieu thereof --<u>pi</u>-deficient--.

UNITED STATES PATENT AND TRADEMARK OFFICE
CERTIFICATE OF CORRECTION

PATENT NO. : 5,002,641
DATED : March 26, 1991
INVENTOR(S) : Joseph E. Toomey, Jr.

It is certified that error appears in the above-indentified patent and that said Letters Patent is hereby corrected as shown below:

In column 14 line 1, please delete "pi-deficient" and insert in Lieu thereof --pi-deficient--.

Signed and Sealed this

Fifteenth Day of June, 1993

Attest:

MICHAEL K. KIRK

Attesting Officer

Acting Commissioner of Patents and Trademarks